United States Patent
Clementz

[11] Patent Number: 5,407,353
[45] Date of Patent: Apr. 18, 1995

[54] EXTRACTOR FOR USE IN DENTAL TREATMENT

[76] Inventor: Pehr Clementz, Logdansvägen 34, Sundbyberg, Sweden, 172 42

[21] Appl. No.: 87,755
[22] PCT Filed: Jan. 21, 1992
[86] PCT No.: PCT/SE92/00032
 § 371 Date: Jul. 6, 1993
 § 102(e) Date: Jul. 6, 1993
[87] PCT Pub. No.: WO92/12686
 PCT Pub. Date: Aug. 6, 1992

[30] Foreign Application Priority Data
Jan. 23, 1991 [SE] Sweden ................. 9100202

[51] Int. Cl.$^6$ ............................ A61C 17/06
[52] U.S. Cl. ........................ 433/93; 433/136
[58] Field of Search ............ 433/91, 93, 94, 116, 433/140, 136; 128/852, 861

[56] References Cited
U.S. PATENT DOCUMENTS

| | | | |
|---|---|---|---|
| 2,637,107 | 5/1953 | Daigle | 433/136 |
| 2,706,334 | 4/1955 | Daigle | 433/93 |
| 3,772,790 | 11/1973 | Swan-Gett et al. | 433/136 |
| 4,975,057 | 12/1990 | Dyfvermark | 433/93 |
| 4,992,046 | 2/1991 | Sharp | 433/93 |

FOREIGN PATENT DOCUMENTS

| | | |
|---|---|---|
| 0137090 | 4/1985 | European Pat. Off. |
| 458012 | 6/1987 | Sweden |

*Primary Examiner*—Cary E. O'Connor
*Attorney, Agent, or Firm*—Jacobson, Price, Holman & Stern

[57] ABSTRACT

An extractor for extracting by suction dust and vapor generated during dental treatment. The device includes a hood-like member (1) which is intended to be placed over the patient's teeth, and a suction device (2) having a suction nozzle located within the hood-like member (1). The hood-like member (1) has a part which faces towards the free ends of the teeth and which is provided with an opening (10) through which dental work can be carried out. The hood-like member is made from a readily-shapable and/or resilient material. Bendable inserts (11, 12, 50) can be placed in or on the walls (41, 42) of the hood-like member, on opposite sides of the opening (10). The part of the suction device located nearest the hood-like member includes a handle (63) by means of which the hood-like member can be placed over and held in position on the patient's teeth.

12 Claims, 2 Drawing Sheets

EXTRACTOR FOR USE IN DENTAL TREATMENT

TECHNICAL FIELD

The present invention relates to an extractor for use in dental treatment.

BACKGROUND ART

It is earlier known to use different kinds of extractors in the course of dental treatment, primarily to remove saliva from the patient's mouth together with water supplied to the patient's mouth during treatment, for instance to cool the drill used to drill a patient's tooth. These extractors may have the form of a helical extractor which is attached to the patient's jaw, or the form of a plastic tube which is held in place by a dental nurse during particularly intensive stages of dental treatment. These extractors may also have the additional function of clamping the patient's tongue or of holding the tongue to one side, so as to avoid injury to the tongue.

Society has become more and more aware of the problems that can be caused by amalgam dental fillings. Dental amalgam is broken down by wear and by corrosion and can cause chronic mercury poisoning, resulting in migraine, dizziness, eczema, and bleeding, among other ailments.

On some occasions, patients have suffered serious, acute poisoning problems when replacing old amalgam fillings with plastic fillings for instance, probably as a result of the mercury vapour and amalgam dust that is generated when drilling-out the fillings. It is important to note that the specific surface area from which mercury vapour can be generated is considerably enlarged when the amalgam is finely-divided in the process of treating a tooth in the aforesaid manner.

Many patients have been caused considerable suffering as a result of prolonged vapourization from amalgam fillings and/or when treating old fillings. It will be also noted that dentists and dental nurses will also be subjected to toxic vapours and toxic dust, in addition to the patients.

The object of the present invention is to endeavour to overcome the aforesaid drawbacks.

DISCLOSURE OF THE INVENTION

The inventive extractor includes a hood-like member which defines a given volume and which is intended to be placed over one or more teeth. The hood-like member includes a part which is turned so as to face towards the free ends of the teeth and which is provided with an opening through which dental treatment can be carried out.

A suction device has a suction nozzle which is located within the hood-like member and which functions to extract dust and vapour generated during treatment of the tooth or teeth concerned.

These and other characteristic features of the inventive extractor are set forth in the following claims.

The hood-like member can be made from a readily-formable, optionally resilient material and is constructed advantageously so that the hood-like member will strive to lie against the patient's gum or against the base part of the patient's teeth. In addition to achieving this desired abutment of the hood-like member by appropriate configuration of the readily-formable material, it can also be achieved by providing the hood-like member with an insert in the form of, e.g., wires or bands which affect the shape of the hood-like member in a manner to achieve said abutment.

That part of the suction device which is located nearest the hood-like member may be given the form of a handle with which said hood-like member can be placed in a suitable position over the tooth or teeth to be located and held in this position. This assumes that the extractor is held in position with one hand, normally by the dentist. The handle can be readily inserted into and removed from the hood-like member, which is suitably intended for one-time-use only and is therefore replaced with each new patient. The handle can be appropriately constructed so as to enable the hood-like member to be held in position without needing to hold the handle. When it is desirable that the extractor will remain in position without requiring assistance, this can be achieved, for instance, by inserting into the hood-like member an insert which will ensure that the hood-like member will abut the patient's gum or the base parts of the patient's teeth, in the aforesaid manner.

BRIEF DESCRIPTION OF THE DRAWING

The present invention will now be described in more detail with reference to the accompanying schematic drawing, in which.

Figure 1:
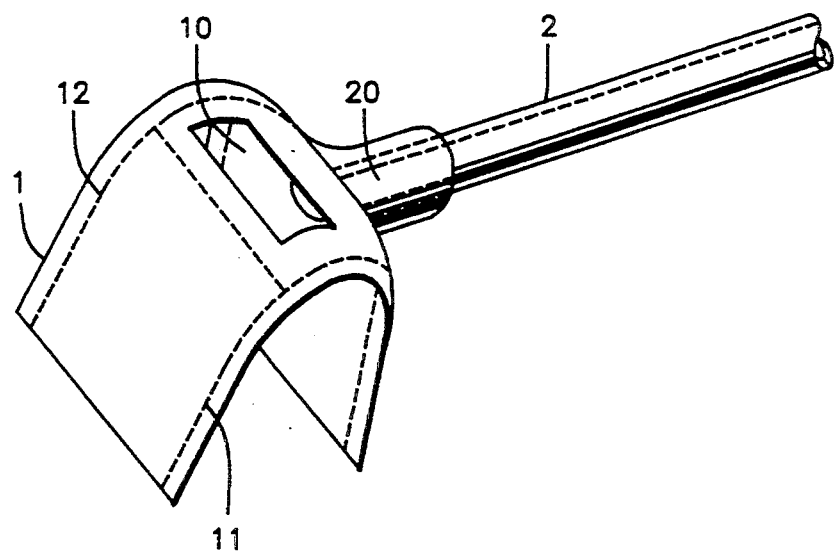
FIG. 1 is a perspective view of an inventive extractor.

The extractor illustrated in FIG. 1 includes a hood-like member 1 which defines a given volume and which is intended to be placed around one or more teeth of a patient. A suction device 2 is connected to the hood-like member 1.

The hood-like member 1 is intended to be placed over the patient's teeth and includes a part which is intended to face towards the free ends of the patient's teeth and which is provided with an opening 10 through which dental work can be carried out when the hood-like member is positioned over teeth in either the upper or lower jaw of the patient.

The suction device includes a suction nozzle 20 which enters the hood-like member 1 and which functions to extract by suction material generated in the form of dust and vapour during dental treatment.

The hood-like member 1 is preferably made of a readily-shapable, resilient material and is provided on opposite sides of the opening 10 with a respective insert 11 and 12 made of a bendable material. This bendable or resilient material may, for instance, have the form of metal wire or rod. The inserts are intended to maintain the shape of the hood-like member and, when necessary, to shape the hood-like member, by mechanical action, in a manner which will ensure given, suitable abutment of the hood-like member against the base parts of the teeth and against corresponding parts of the gum.

That part of the suction device 2 which is located nearest the hood-like member 1 includes a handle by means of which the hood-like member can be held securely in position around the teeth being treated, subsequent to placing the hood-like member in position. The handle can be readily inserted into and removed from the hood-like member 1, and the hood-like member is preferably intended for one-time-use only, and is thus replaced with each new patient.

Practical tests have shown that the inventive extractor will remove both dust and vapour generated when drilling old fillings very effectively, and that the extractor also guards against the patient's tongue coming into contact with the drill used in the dental treatment.

Figure 2:
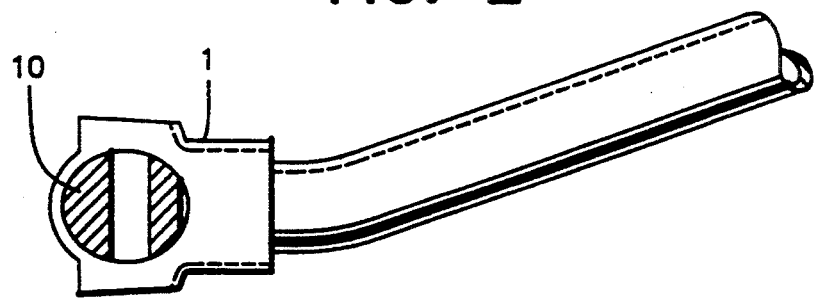
FIG. 2 illustrates another embodiment of the inventive extractor from above.
Figure 3:
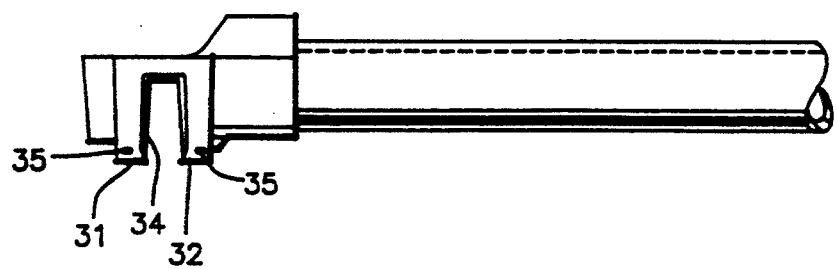
FIG. 3 is a side view of the second embodiment of said extractor.
Figure 4:
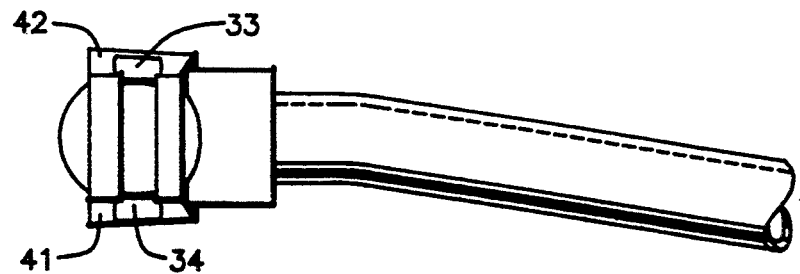
FIG. 4 is a view of the second embodiment of the extractor from beneath.

The embodiment of the extractor illustrated in FIGS. 2-4 includes a hood-like member 1 which is made from a shapable and/or resilient material. The ends 31, 32 (see FIG. 3) of the hood-like member 1 remote from the opening 10 have mutually parallel edges which face inwardly towards one another and the hood-like member in general is formed so that the edges will endeavour to lie in abutment with the patient's gum and/or the base parts of respective teeth when in use. The opening 10 has a circular or oval shape.

Figure 5:
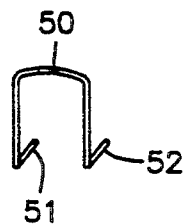
FIG. 5 illustrates a U-shaped insert intended to be placed on the walls of the hood-like member according to the second embodiment.

U-shaped, bendable wire devices 50 (see FIG. 5) are placed on the side surfaces 41, 42 of the hood-like member (see FIG. 4) so that the hood-like member can be brought into firm abutment with the patient's gum, etc., by pressing the edges 31, 32 in towards one another. The wire device has bent ends 51, 52 which are inserted into holes 35 provided in the hood-like member 1.

The ends 51, 52 of the two U-shaped wire devices 50 may be connected together pair-wise means of transverse wires placed in the ends 31, 32 of the hood-like member 1 (at right angles to the plane of the paper in FIG. 3).

As will be seen from FIGS. 3-4, the hood-like member 1 is provided with stiffenings or reinforcements 33, 34 (outwardly-projecting edges) in the vicinity of the walls 41, 42.

The hood-like member 1 may be made of environmentally-friendly material, such as cellulose, rubber and plastic material.

Figure 6:
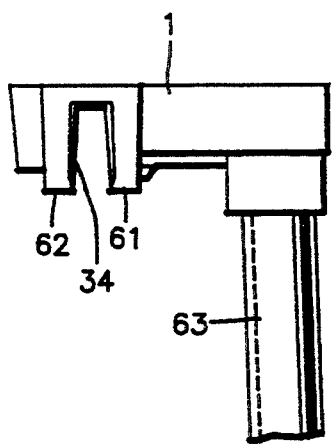
FIG. 6 illustrates a modification of the extractor according to the second embodiment.

The modified extractor illustrated in FIG. 6 has two generally parallel flank parts 61, 62 which extend from that part of the hood-like member 1 which is provided with the opening 10 (see FIG. 2). That part of the suction device 2 located nearest the hood-like member 1 has the form of a handle 63 by means of which the hood-like member one can be placed in position over the patient's teeth during dental treatment. The handle 63 extends essentially in the same direction as the flank parts 61, 62. This modified version of the extractor can be held in position without needing to hold the device manually, in those instances when the patient is treated in an essentially recumbent position, which is the normal position of the patient in modern dental treatment.

Figure 7:
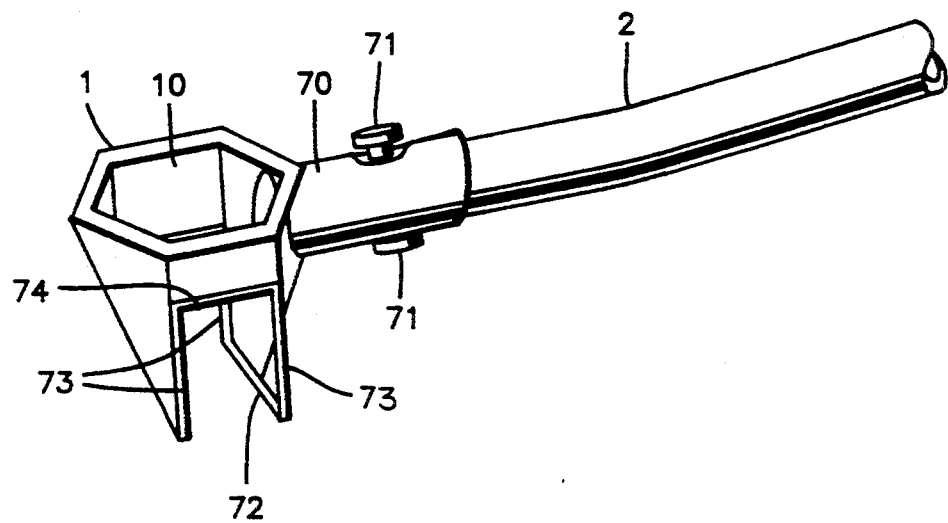
FIG. 7 is a perspective view of a third embodiment of the inventive extractor.

The extractor shown in FIG. 7 includes a hood-like member 1 having a piece of pipe 70 adapted to be manually pushed over the outer end of a suction conduit 2. At least one protrusion 71 on the suction conduit is adapted to snap into or extend through a corresponding opening in the piece of pipe 70, to prevent an unintentional disconnection of the hood-like member 1 from the conduit 2. The hood-like member 1 shown has a hexagonal access opening 10 and is provided with thin sealing ribs 72, 73, 74 of plastics material, for instance, which will extend along the gum and tooth surfaces and cause the hood-like member 1 to sealingly engage arround teeth and gums.

I claim:

1. An extractor for use in dental treatment, said extractor comprising:
a hood-like member to be placed over one or more teeth of a patient and which defines a given volume around said tooth or teeth, said hood-like member including a part to face towards the free ends of the teeth and which is provided with an opening through which dental work can be carried out, and a suction device having a nozzle for entering the hood-like member and which functions to extract by suction material in the form of dust and vapour generated during said dental work, and hood-like member being made from a material having at least one of the properties of readily-shapable and resilient and being constructed so that it will strive to lie in abutment with the patient's gum or with the base parts of the patient's teeth.

2. An extractor according to claim 1, wherein the hood-like member includes elongated inserts which act on the hood-like member to cause said member to lie in abutment with the patient's gum or the base parts of the patient's teeth.

3. An extractor according to claim 2, wherein the elongated inserts are placed on opposite sides of the opening so as to maintain the shape of the hood-like member and, when necessary, to shape the hood-like member appropriately so as to achieve said abutment, by mechanical action.

4. An extractor according to claim 1, wherein bendable U-shaped wire elements are placed on the hood-like member on opposite sides of the opening and ends of said wire elements are bent and secured to the hood-like member.

5. An extractor according to claim 1, wherein a part of the suction device located nearest the hood-like member includes a handle for placing the hood-like member over the patient's teeth during dental treatment.

6. An extractor according to claim 1, wherein the hood-like member includes two generally plane-parallel flank parts extending from said part provided with an opening and a part of the suction device located nearest the hood-like member includes a handle for placing the hood-like member over the patient's teeth during dental treatment, said handle extending generally parallel with the flank parts.

7. An extractor for use in dental treatment, said extractor comprising:
a hood-like member to be placed over one or more teeth of a patient and which defines a given volume around said tooth or teeth, said hood-like member including a part to face towards the free ends of the teeth and which is provided with an opening through which dental work can be carried out, and a suction device having a nozzle for entering the hood-like member and which functions to extract by suction material in the form of dust and vapour generated during said dental work, said hood-like member including elongated inserts which act on the hood-like member to cause said member to lie in abutment with the patient's gum or the base parts of the patient's teeth.

8. An extractor according to claim 7, wherein a part of the suction device located nearest the hood-like member includes a handle for placing the hood-like member over the patient's teeth during dental treatment.

9. An extractor for use in dental treatment, said extractor comprising:
   a hood-like member to be placed over one or more teeth of a patient and which defines a given volume around said tooth or teeth, said hood-like member including a part to face towards the free ends of the teeth and which is provided with an opening through which dental work can be carried out,
   a suction device having a nozzle for entering the hood-like member and which functions to extract by suction material in the form of dust and vapour generated during said dental work, and
   bendable U-shaped wire elements placed on the hood-like member on opposite sides of the opening, ends of said wire elements being bent and secured to the hood-like member.

10. An extractor according to claim 9, wherein a part of the suction device located nearest the hood-like member includes a handle for placing the hood-like member over the patient's teeth during dental treatment.

11. An extractor for use in dental treatment, said extractor comprising:
    a hood-like member to be placed over one or more teeth of a patient and which defines a given volume around said tooth or teeth, said hood-like member including a part to face towards the free ends of the teeth and which is provided with an opening through which dental work can be carried out, and a suction device having a nozzle for entering the hood-like member and which functions to extract by suction material in the form of dust and vapour generated during said dental work, said hood-like member including two generally plane-parallel flank parts extending from said part provided with an opening and a part of the suction device located nearest the hood-like member includes a handle for placing the hood-like member over the patient's teeth during dental treatment, said handle extending generally parallel with the flank parts.

12. An extractor according to claim 11, wherein a part of the suction device located nearest the hood-like member includes a handle for placing the hood-like member over the patient's teeth during dental treatment.

* * * * *